US00PP25894P3

(12) United States Plant Patent
Uquillas

(10) Patent No.: US PP25,894 P3
(45) Date of Patent: Sep. 15, 2015

(54) GRAPEVINE PLANT DENOMINATED 'INIAGRAPE-ONE'

(50) Latin Name: ***Vitis vinifera* L.**
Varietal Denomination: Iniagrape-one

(75) Inventor: Carolina Uquillas, Santiago (CL)

(73) Assignee: INSTITUTO DE INVESTIGACIONES AGROPECUARIAS, Providencia, Santiago (CL)

( * ) Notice: Subject to any disclaimer, the term of this patent is extended or adjusted under 35 U.S.C. 154(b) by 0 days.

(21) Appl. No.: 13/554,669

(22) Filed: Jul. 20, 2012

(65) Prior Publication Data

US 2013/0025004 A1 Jan. 24, 2013

(30) Foreign Application Priority Data

Jul. 22, 2011 (CL) ..... 1148

(51) Int. Cl.
*A01H 5/00* (2006.01)
*A01H 5/08* (2006.01)

(52) U.S. Cl.
USPC ..... Plt./205
CPC ..... *A01H 5/0812* (2013.01)

(58) Field of Classification Search
USPC ..... Plt./205
See application file for complete search history.

(56) References Cited

U.S. PATENT DOCUMENTS

PP22,322 P3 12/2011 Kamiel et al.

OTHER PUBLICATIONS

David W. Ramming, "'Thomcord' Grape", HortScience, vol. 43, No. 3, pp. 945-946, 2008.
Richard L. Emershad et al., "In-Ovulo Embryo Culture of *Vitis vinifera* L.C.V. 'Thompson Seedless'", Amer. J. Bot., vol. 71, No. 6, pp. 873-877, 1984.
Richard L. Emershad et al., "In Ovulo Embryo Development and Plant Formation from Stenospermic Genotypes of *Vitis vinifera*", Amer. J. Bot., vol. 76, No. 3, pp. 397-402, 1989.

*Primary Examiner* — Annette Para
(74) *Attorney, Agent, or Firm* — Greer, Burns & Crain, Ltd.

(57) ABSTRACT

A new and distinct variety of grapevine denominated 'Iniagrape-one' which is characterized by its midseason ripening. Its fruit is attractive blue-black, with seed rudiments, broad ellipsoid-narrow ellipsoid fruit shape, difficult berry separation from pedicel, firm texture with very good particular flavor because its acidity and sugars-acid ratio. The clusters are large in size, conical and medium density. Good productive capacity and keeping and shipping quality.

4 Drawing Sheets

Latin name: *Vitis vinifera* L.
Varietal denomination: Iniagrape-one.

BACKGROUND AND SUMMARY OF THE INVENTION

The present invention relates to the discovery and asexual propagation of a new variety of grapevine, *Vitis vinifera* L. denominated Iniagrape-one. This new cultivar resulted from controlled hybridization between Flame Seedless (♀) and Black Seedless (♂) varieties performed in 1998 at Santiago Chile (latitude 33° 34,32 S, longitude 70° 37,41 S, altitude 631 meters above sea level), corroborated by molecular markers techniques. Plants were produced from maternal parent Flame Seedless using embryo rescue procedures (Emershad and Ramming, Amer. J. Bot. (1984), 71:873-877; Emershad et al., Amer. J. Bot. (1989), 76:397-402; Ramming, HortScience (2008) 43(3):945-946). The original vine was planted in 2000 at La Platina Experiment Research Center in Santiago Chile, and selected in 2004.

'Iniagrape-one' is vigorous and produces a strong vine when grafted on Freedom or Harmony rootstocks. Cane or spur pruning may be used because of its high bud fruitfulness along the shoots. In the central area of Chile (Aconcagua Valley 32° 52 S, 70° 38 W)), budbreak occurs around September 22$^{nd}$, and flowering around November 15$^{th}$.

This behavior is similar to Autumn Royal cultivar. The clusters are large in size, about 600-800 gr., conical and medium density. The fruit has a good export market potential for having good keeping and shipping quality.

The berries are dark blue, and according with the Colour Chart of The Royal Horticulture Society (R.H.S.) belongs to the Blue Group N° 103A. They are ellipsoid in shape, reaching a diameter of 20-22 mm and about 8 gr per berry when sprayed with gibberellic acid. They normally contain 2 to 3 rudimentary soft seed traces per berry and depending on the location and the season, occasionally present some few berries containing 1 fully developed seed. This behavior is similar to the cultivar Autumn Royal. The clusters are large in size, about 600-800 gr., conical and medium density. The fruit has a good export market potential for having good keeping and shipping quality.

'Iniagrape-one' is harvested in the middle of February in the central area of Chile (Aconcagua Valley 32° 52 S, 70° 38 W)), around one week after Black Seedless and Midnight Beauty and 3-4 before Autumn Royal cultivar. 'Iniagrape-one' differs from those varieties for its complete uniform dark blue color without the need for any hormonal spray to induce pigmentation. It has a distinct particular good flavor given by its good sugar acidity at harvest time (19-21° brix and 0.9-1% acidity). It also differs from Black Seedless for having better keeping and shipping quality. The new variety has no problem of shattering during harvest or post-harvest due to a difficult separation of the berry pedicel. For the variety Midnight Beauty separation of the berry pedicel has been classified as medium, and in Autumn Royal the union between the rachis and the pedicel is fragile, and berries can be separated from the rachis during harvesting. Unlike Autumn Royal, 'Iniagrape-one' has no tendency to crack.

ASEXUAL PROPAGATION

The new 'Iniagrape-one' variety has shown to maintain its distinguishing characteristics through successive asexual propagation. The asexual propagation has been done either by rooting cuttings or by grafting scions onto different rootstocks. This asexual propagation has taken place at the INIA Experimental Station of La Platina located in Santiago, Chile, latitude 33° 34,32 S, longitude 70° 37,41 S, altitude 631 meters above sea level. Experimental plantations using this variety have been done in different Experimental Stations of INIA located in different sites of North and Central regions of Chile.

BRIEF DESCRIPTION OF THE FIGURES

The drawings of the grapevine of the present invention are color photographs as follows.

Description applies to vines grafted onto rootstock Freedom.

DETAILED BOTANICAL DESCRIPTION

The following botanical description represents a three season evaluation observed in an approximately four to six years old grapevine. In all sites, vines are cane pruned on an overhead trellis system (grape arbor) and the descriptive data are from natural non thinned and commercial handled clusters.

LEAVES

Figure 1:
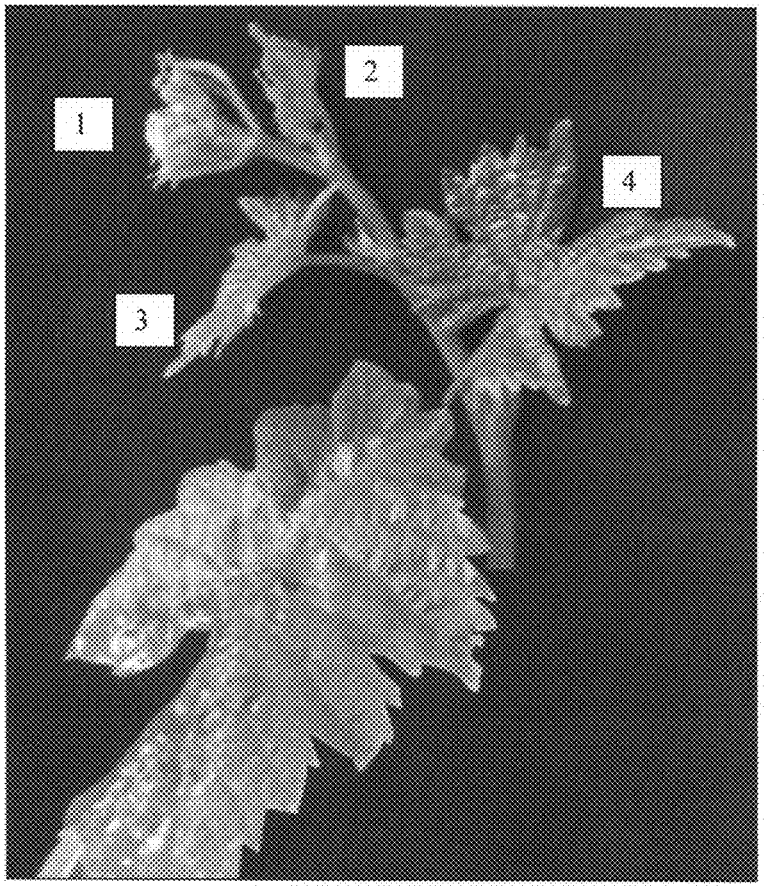
FIG. 1: A shoot with young leaves numerated after the IPGRI, UPOV, OIV 1997 manual.

Young leaves: Recorded on the first 4 distal unfolded leaves. After IPGRI, UPOV & OIV 1997 (please see FIG. 1)

TABLE 1

Young leaf characteristics

| Young leaves N° | Leaf size (cm) Length | Leaf size (cm) Width | Petiole length (cm) |
|---|---|---|---|
| 1 | 0.98 ± 0.1 | 1.08 ± 0.17 | 0.26 ± 0.08 |
| 2 | 1.85 ± 0.31 | 2.0 ± 0 53 | 0.5 ± 0.18 |
| 3 | 2.4 ± 0.49 | 3.0 ± 0.41 | 3.0 ± 0.41 |
| 4 | 3.5 ± 0.7 | 4.0 ± 0.75 | 4.0 ± 0.75 |

| Young leaves | Color surface (After RHS Colour Chart) | | Density of hairs between veins at lower surface | |
|---|---|---|---|---|
| N° | Upper surface | Lower surface | Postrated | Erect |
| 1 | FAN3 YELLOW GREEN GROUP N 144A | FAN3 YELLOW GREEN GROUP N 144A | Absent | Absent |
| 2 | FAN3 YELLOW GREEN GROUP N 144A | FAN3 YELLOW GREEN GROUP N 144A | Absent | Absent |
| 3 | FAN3 YELLOW GREEN GROUP N 145A | FAN3 YELLOW GREEN GROUP N 145A | Absent | Absent |
| 4 | FAN3 YELLOW GREEN GROUP N 144C | FAN3 YELLOW GREEN GROUP N 144C | Absent | Absent |

Figure 2:
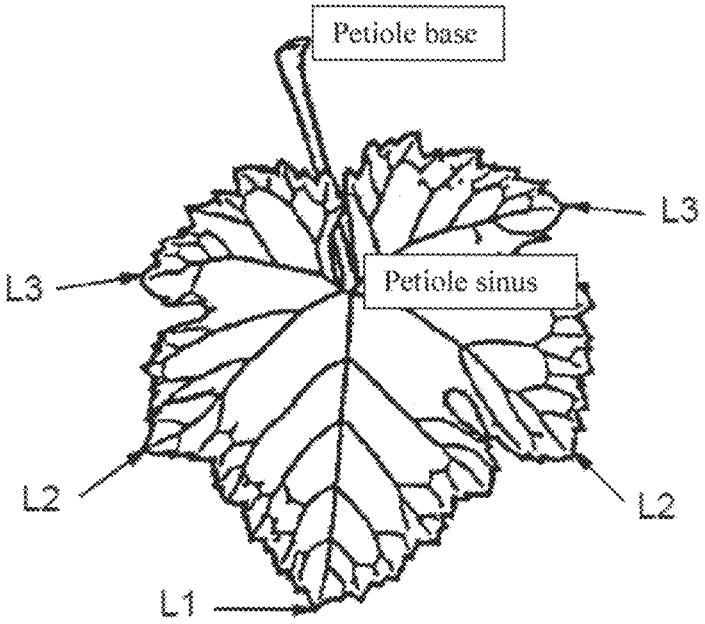
FIG. 2: A typical five lobes leaf after the IPGRI, UPOV, OIV 1997 manual.
Figure 3:
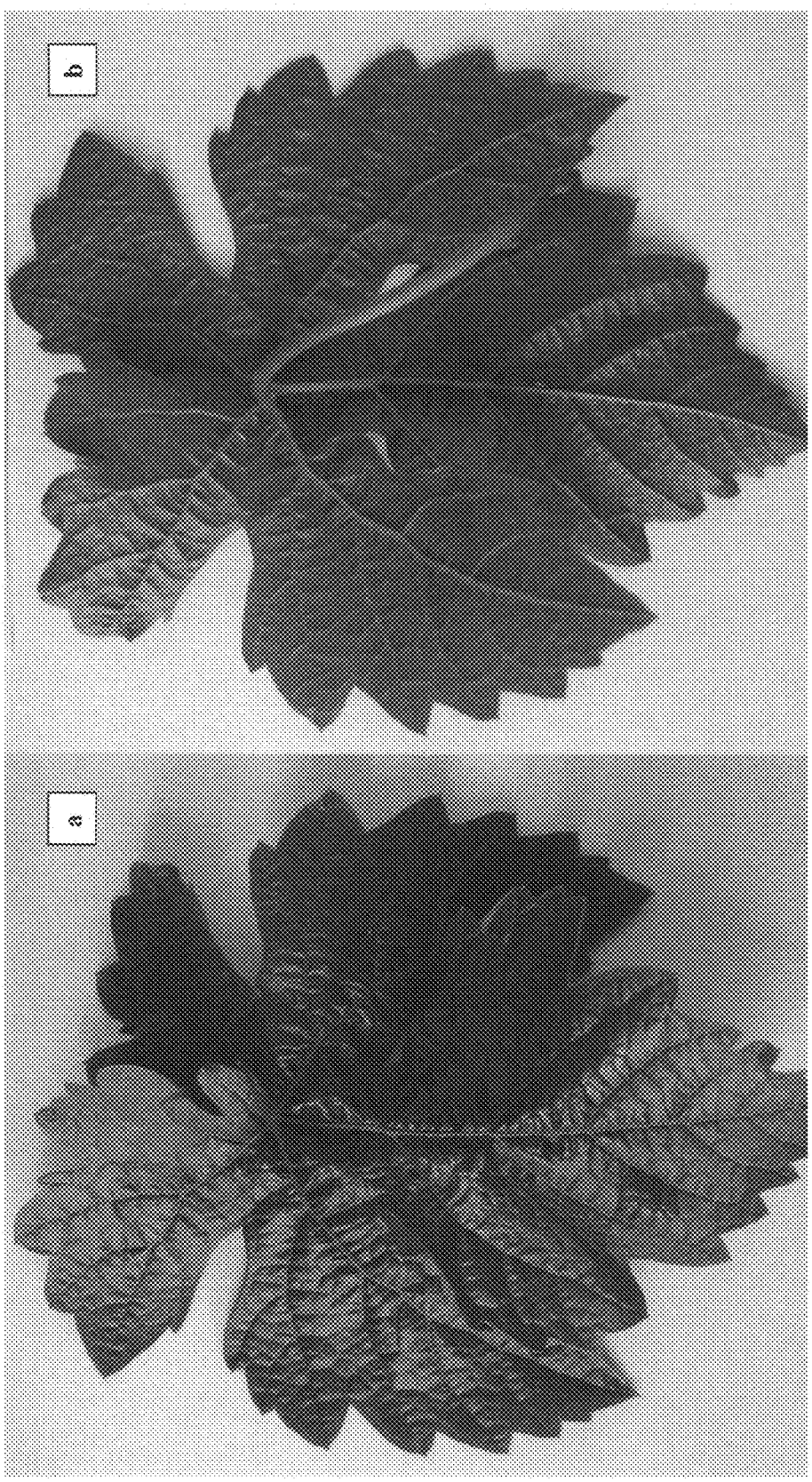
FIG. 3: (a) The upper surface; (b) the lower surface of a mature leaf.
Figure 4:
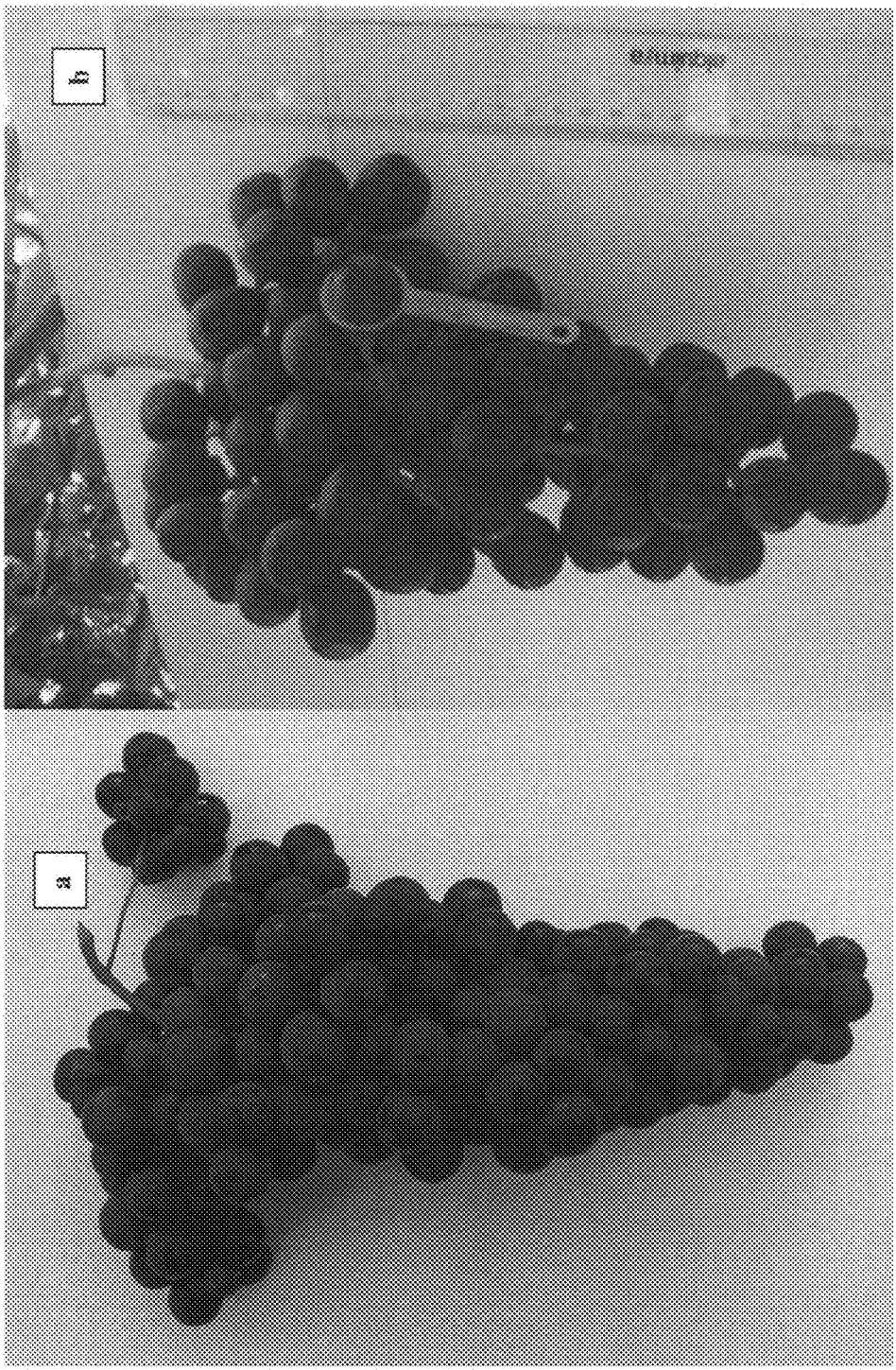
FIG. 4: (a) A non thinned cluster of Iniagrape-one showing the typical false shoulder. (b) A commercially handled cluster (120 berries/cluster).

Mature leaves: For interpretation please see FIG. 2

TABLE 2

Mature leaf characteristics

| Type of leaf | Length (cm) From petiole sinus to the tip of lobe $L_1$ | Length (cm) From petiole base to the tip of lobe $L_1$ | Width (cm) Measured between tips of both $L_2$ lobes | Size of blade After IPGRI, UPOV & OIV 1997 | Shape of Blade After IPGRI, UPOV & OIV 1997 |
|---|---|---|---|---|---|
| Sunny | 10.5 | 16.5 | 15.5 | Medium | Pentagonal |
| Shaded | 12.0 | 18.5 | 18.8 | Big | Pentagonal |
| Average | 11.3 | 17.5 | 17.2 | Medium-Big | Pentagonal |

*Number of lobes.*—5.

*Anthocyanin coloration of main veins on the upper side of the blade.*—Medium.

*Mature leaf profile.*—Undulate.

*Blistering surface of blade upper surface.*—Weak.

*Shape of teeth.*—Both sides convex.

*Length of teeth.*—0.47±0.09 cm.

*Width of teeth.*—0.80±0.12 cm.

*Ratio length/width of teeth.*—0.59±0.13 cm.

*General shape of petiole sinus.*—Lobes slightly overlapped.

*Tooth at petiole sinus.*—Absent.

*Petiole sinus limited by veins.*—Absent.

*Shape of upper lateral sinus.*—Lobes slightly overlapped.

*Depth of upper lateral sinus.*—Deep.

*Prostrate hairs between veins on lower surface of blade.*—Absent or very sparse.

*Erect hairs between veins on lower surface of blade.*—Absent.

*Density of prostrate hairs on main veins on lower surface of blade.*—Very sparse.

*Density of erect hairs on main veins on lower surface of blade.*—Absent or very sparse.

*Prostrate hairs on main veins on upper surface of blade.*—Absent.

*Petiole length of mature leaf.*—10.8±1.62 cm.

*Basal petiole diameter of mature leaf.*—0.62±0.13 cm.

*Color upper surface.*—RHS FAN3 GREEN GROUP 137 A.

*Color lower surface.*—RHS FAN3 GREEN GROUP 137 D.

FLOWERS

General:

*Flower sex*.—Perfect.

*Position of first flowering node*.—From 3rd node.

*Number of inflorescences per shoot*.—About 1 to 2.

*Date of full bloom*.—Around November 15$^{th}$, Central valley of Chile.

*Duration of bloom period*.—On average, about 7 days.

*Time of bloom*.—Medium, around, November 8$^{th}$, Central valley of Chile.

*Calyptra color*.—RHS FAN3 YELLOW GREEN GROUP N144C.

*Ovary color*.—RHS FAN3 GREEN GROUP N134 A.

*Stamens*.—Erect.

*Pistil*.—Well developed.

FRUIT

General:

*Ripening period*.—Midseason. About one week after of "Black Seedless" and "Midnight Beauty" and three to four weeks ahead "Autumn Royal" in the growing area of Aconcagua valley (Los Andes), Chile.

*Use*.—Fresh market.

*Keeping quality*.—Good.

*Shipping quality*.—Good.

*Date of first harvest*.—Feb. 19, 2007. in the growing area of Aconcagua valley (Los Andes), Chile.

*Solids-sugar*.—Refractometer test about 19-21° Brix.

*Acid*.—Acid about 0.9-1%.

*Juice pH*.—About 3.5.

*Sugar/acid ratio*.—About 20.

*Tendency to crack*.—None.

*Sensitivity to sunburn*.—None.

Cluster:

*Bunch size* (*peduncle excluded*).—Large.

*Bunch length* (*peduncle excluded*).—About 19-20 cm.

*Bunch width*.—About 15-17 cm.

*Bunch weight*.—Between 600-800 gr.

*Bunch density*.—Medium.

*Number of berries per cluster* (*average*).—Non thinned cluster: 375.7±25.4. Thinned cluster: 125.8±31.4.

*Form*.—Conical.

Peduncle:

*Length of peduncle*.—6.5 cm from insertion to the first true shoulder.

*Lignification of peduncle*.—Medium.

*Peduncle color*.—RHS FAN 1 ORANGE RED GROUP N34 D.

Berry:

*Size*.—Large.

*Uniformity of size*.—Medium.

*Berry weight*.—About 8 gr per berry.

*Shape*.—Broad ellipsoid and narrow ellipsoid.

*Presence of seeds*.—Rudimentary. Berries containing 2 to 3 rudimentary soft seed traces. Occasionally, depending on location and the season, some few berries contain 1 fully developed seed.

*Cross section*.—Circular.

*Dimensions*.—Longitudinal axis about 24 mm; horizontal axis about 22 mm.

*Skin color* (*without bloom*).—RHS, FAN 2 BLUE GROUP 103 A.

*Flesh color*.—RHS, FAN 3 YELLOW GREEN GROUP 151-A.

*Juiciness of flesh*.—Juicy.

*Berry firmness*.—Firm.

*Particular flavor*.—Other than Muscat, foxy or herbaceous.

*Bloom* (*cuticular wax*).—Medium.

*Pedicel length*.—About 10 mm.

*Berry separation from pedicel*.—Difficult.

Skin:

*Thickness*.—Thick, about 0.5 mm.

*Texture*.—Smooth.

*Reticulation*.—Absent.

*Roughness*.—Absent.

Seed:

Presence of seeds: According to observations of three productive seasons and three different locations, the variety was phenotypically classified as rudimentary. The berries contain 1 to 3 red rudimentary soft seed trace per berry. Occasionally, depending on location and the season, some few berries contain 1 well developed seed.

VINE

General:

*Size*.—Large.

*Vigor*.—Vigorous.

*Density of foliage*.—Dense.

*Productivity*.—Very productive, about 24 to 27 Kg/vine.

*Root stock*.—Freedom.

CANES

Young shoot:

*Form of tip*.—Fully open.

*Intensity of anthocyanin coloration of tip*.—Absent or very weak.

*Density of prostrate hairs on tip*.—Medium.

*Density of erect hairs on tip*.—Absent or very sparse.

Shoot:

*Attitude during flowering on shoot which are not tied*.—Semi-erect.

*Color of dorsal side of internodes*.—Green RHS FAN 3 YELLOW GREEN GROUP 152 B.

*Color of ventral side of internodes*.—Green and red striped. RHS FAN3 YELLOW GREEN GROUP 144 B.

*Color of dorsal side of node*.—RHS STRIPS OF FAN1 RED GROUP 53 C.

*Color of ventral side of nodes*.—RHS FAN 3 YELLOW GREEN GROUP 144 B and red striped.

*Density of erect hairs on nodes*.—Absent or very sparse.

*Erect hairs on internode*.—Absent or very sparse.

*Density of prostrate hairs on nodes*.—Absent or very sparse.

*Density of prostrate hairs internodes*.—Absent or very sparse.

Woody shoot:

*Internode length*.—Short or medium, about 5.5 to 13.0 cm.

*Cross section*.—Circular.

*Surface texture*.—Smooth.

*Main color*.—RHS FAN 1 ORANGE RED GROUP 34 D.

Buds:

*Cane bud fruitfulness*.—Basal most fruitful.

*Time of bud burst*.—September 22$^{nd}$, Central area.

Tendrils:

*Length of tendrils*.—Long, 24.97±3.15.

REFERENCES

1. Emershad, R. L. and D. W. Ramming. 1984. In-ovulo embryo culture of *Vitis vinifera* L. cv. 'Thompson Seedless'. Amer. J. Bot. 71:873-877.
2. Emershad, R. L. and D. W. Ramming, and M. D. Serpe. 1989. In-ovulo embryo development and plant formation from stenospermic genotypes of *Vitis vinifera*. Amer. J. Bot. 76:397-402.
3. IPGR, UPOV, OIV, 1997.—Descriptors for grapevine (*Vitis* spp.) International Union for the Protection of New Varieties of Plants. Geneva, Switzerland/Office International de la Vigne et du Vin, Paris, France/International Plant Genetic Resources Institute, Rome, Italy. ISBN 92-9043-352-3
4. Ramming, D. W. 2008. 'Thomcord' Grape.HortScience 43(3):945-946.
5. Royal Horticultural Society 2007. The Royal Horticultural Society's Colour Chart, Fifth edition, London.

Having thus described and illustrated the new variety of grapevine, I claim:

1. A new and distinct variety of grapevine as herein illustrated and described.

* * * * *